United States Patent [19]

Chartrain et al.

[11] Patent Number: 5,523,233

[45] Date of Patent: Jun. 4, 1996

[54] ENZYMATIC HYDROLYSIS OF 3,3-DIETHYL-4-[(4-CARBOXY)PHENOXY]-2-AZETIDINONE ESTERS

[75] Inventors: Michel M. Chartrain, Westfield; Raymond Cvetovich, Scotch Plains; Christopher Roberge, Clark, all of N.J.

[73] Assignee: Merck & Co., Inc., Rahway, N.J.

[21] Appl. No.: 433,586

[22] Filed: May 3, 1995

[51] Int. Cl.$^6$ .................................................. C12P 41/00
[52] U.S. Cl. .................................................. 435/280; 435/875
[58] Field of Search .................................. 435/280, 875

[56] References Cited

U.S. PATENT DOCUMENTS 5,229,381  7/1993  Doherty et al. ........................ 514/210
5,241,064  8/1993  Murata et al. ........................ 540/362

FOREIGN PATENT DOCUMENTS 0337549  4/1989  European Pat. Off. .
0595557  10/1993  European Pat. Off. .

OTHER PUBLICATIONS

C. Marcin, et al, Journal of Industrial Microbiology, 12 (1993) 29–34 (1993) 29–34 (1993) 29–34.
L. Katz, et al, Journal of Industrial Microbiology, 11 (1993) 89–94.
M. Chartrain, et al, Enzyme Microb. Technol., 15 (1993) 575–580.
M. Chartrain, et al, Journal of Fermentation and Bioengineering, vol. 76, No. 6, 487–492 1993.
K. E. Goklen, et al, Bioprocess Engineering 11 (1994) 49–56.

*Primary Examiner*—Irene Marx
*Assistant Examiner*—S. Saucier
*Attorney, Agent, or Firm*—Mollie M. Yang; David L. Rose

[57] ABSTRACT

The present invention relates to a process for converting a racemic mixture of 3,3-diethyl-4-[(4-carboxy)phenoxy]-2-azetidinone esters into the corresponding (S)-acid using lipase derived from Pseudomonas sp. The process provides the target acid in high enantiomeric excess.

4 Claims, No Drawings

ENZYMATIC HYDROLYSIS OF 3,3-DIETHYL-4-[(4-CARBOXY)PHENOXY]-2-AZETIDINONE ESTERS

BACKGROUND OF THE INVENTION

European Published Application 595,557 (published May 4, 1994) discloses novel substituted azetidinones of the general formula 1 as potent elastase inhibitors, which are useful as anti-inflammatory and anti-degenerative agents. These compounds may be used in the treatment of inflammatory conditions resulting in connective tissue destruction, e.g. rheumatoid arthritis, emphysema, bronchial inflammation, chronic bronchitis, glomerulonephritis, osteoarthritis, spondylitis, lupus, psoriasis, atherosclerosis, sepsis, septicemia, shock, myocardial infarction, reperfusion injury, periodonitis, cystic fibrosis and acute respiratory distress syndrome.

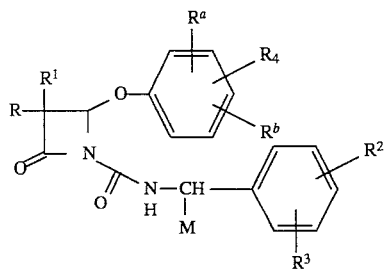

A subset of compounds disclosed in EP 595,557 are those wherein R and $R^1$ are each ethyl, $R_4$ is a carboxylic acid derivative such as a carboxamide, and the absolute configuration at carbon-4 of the azetidinone ring is S (1a)

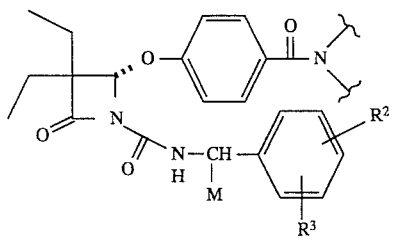

These compounds are exemplified by the compound of formula 2.

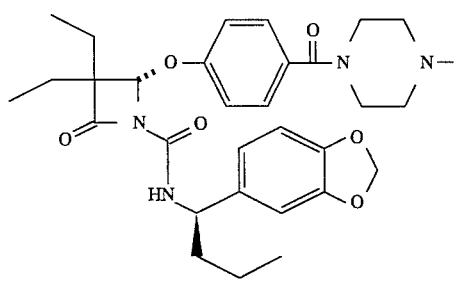

The synthesis of compounds of formula 1 a requires the chiral intermediate of formula I

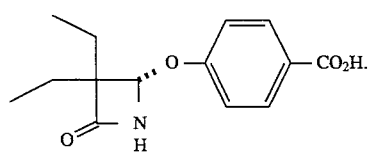

The chiral compound I may be obtained from a racemic mixture using conventional chemical process such as by formation of a salt with an optically active base, followed by separation of the resultant diastereomers, for example by fractional crystallization. However, the chemical resolution process is generally long and tedious, and it would be advantageous if a more convenient method is available for the preparation of chiral compound I.

SUMMARY OF THE INVENTION

The present invention provides an enantioselective process for the preparation of (4S)-3,3-diethyl-4-[(4-carboxy)phenoxy]-2azetidinone from a racemic mixture of a corresponding ester.

DETAILED DESCRIPTION OF THE INVENTION

The present invention concerns enzymatic hydrolysis of ester to produce optically active acid with high enantiomeric excess. More particularly, the present invention provides a novel process for the preparation of the (S)-enantiomer of the azetidinone acid of formula I:

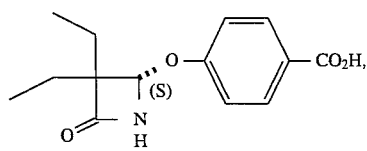

which comprises contacting a racemic mixture of an azetidinone ester of formula II

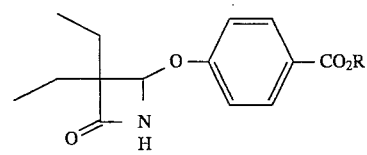

wherein R is selected from the group consisting of benzyl, and $C_1-C_8$ alkyl, with a lipase obtained from Pseudomonas sp., and recovering said (S)-azetidinone acid.

In a preferred embodiment, R of the compound of formula II is benzyl, methyl, propyl or hexyl.

In another preferred embodiment the lipase is the lipoprotein lipase PS available from Amano International Enzyme Co. (Troy, Va., U.S.A.). More preferably, R is benzyl.

In another preferred embodiment, the lipase is derived from Pseudomonas MB5001 (ATCC 55162 ).

In a further preferred embodiment, the enzymatic hydrolysis is carried out in the presence of a surfactant; more preferably the surfactant is a nonionic surfactant such as alkylaryl polyether alcohols, for example octylphenoxy polyethoxyethanol such as Triton®X-100 (available from Sigma Chemical Co.).

The process of the present invention provides an efficient method for the preparation of a compound of formula I with high optical purity.

Preparation of the Substrates

The substrates, azetidinone esters of formula II, can be prepared according to the general process disclosed in US Patent 5,229,381, and as shown schematically below using the benzyl ester as an example.

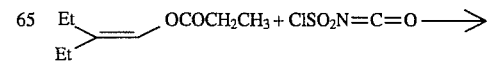

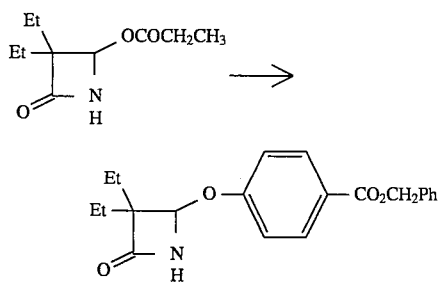

Thus 2,2-diethylvinyl propionate and chlorosulfonyl isocyanate are reacted to provide a racemic mixture of 3,3-diethyl-4-propionyloxy-2-azetidinone. This propionate is then reacted with benzyl 4-hydroxybenzoate in the presence of a base such as sodium hydroxide to provide 3,3-diethyl-4-[(4-benzyloxycarbonyl)phenoxy]-2-azetidinone.

Sources of the Lipases

The process of the present invention may be carried out using a lipase derived from Pseudomonas sp. The present inventors have discovered two preferred lipases that are capable of effecting the stereoselective hydrolysis of compounds of formula II to provide the (S)-enantiomer of formula I. One such lipase is obtained from *Pseudomonas aeruginosa* MB 5001, which has been deposited in accordance with the Budapest Treaty with the American Type Culture Collection, 12301 Parklawn Drive, Rockville, Md. as ATCC No. 55162 on Mar. 26, 1991 and in the Merck Culture Collection as MB 5001. The production, isolation, purification and characterization of the lipase from this organism has been reported in the following articles:

(1) Chartrain, M. et al "Purification and characterization of a novel bioconverting lipase from *Pseudomonas aeruginosa* MB 5001" *Enzyme Microb. Technol.*, 1993, 15:575–580.

(2) Katz L. et al "Screening and selection of a microbial lipase for the stereospecific hydrolysis of Verlukast" *J. Indust. Microbiology*, 1993, 11:89–94.

(3) Marcin C. et al "Optimization of lipase production by *Pseudomonas aeruginosa* MB 5001 in batch cultivation" *J. Indust. Microbiology*, 1993, 12:29–34.

(4) Chartrain M. et al "Enhancement of lipase production during fedbatch cultivation of *Pseudomonas aeruginosa* MB5001" *J. Fermentation and Bioengineering*, 1993, 76:487–492.

(5) Goklen, K. E. et al "Development of crossflow filtration processes for the commercial-scale isolation of a bacterial lipase" *Biopocess Engineering*, 1994, 11:49–56.

The second preferred lipase useful in the present method is the commercially available lipase preparation derived from Pseudomonas sp., and sold under the Amano label as lipase PS (Amano International Enzyme Co., Inc., Troy, Va.).

Stereoselective Hydrolysis of Ester

The enzymatic hydrolysis of the ester of formula II is carried out under conditions that do not impact unduly on the enzymatic activity of the lipase, or otherwise interfere with the production of the desired final product. Thus, the reaction is conducted in a slightly alkaline environment such as in a buffered solution having pH of about 6.5 to about 9.0; typically, a phosphate buffer of about pH 7.7 is used. The reaction temperature may be from about 25° C. to about 50° C., but preferably at about 37° C. to about 40° C. A surfactant is added to the reaction mixture to solubilize the substrate; preferred surfactants are nonionic surfactants such as alkylaryl polyether alcohols and the like; a more preferred surfactant is octylphenoxy polyethoxyethanol available under the name Triton® X-100 (from Sigma Chemical Co.). The reaction mixture is agitated to ensure contact of the substrate with the enzyme. The enzymatic hydrolysis is allowed to proceed for a period sufficient to generate satisfactory quantity of the desired (S)-azetidinone acid in satisfactory optical purity; typically, the time period is about 72 to about 96 hours; preferably about 96 hours. The amount of the desired acid produced and the optical activity may be monitored by HPLC and chiral HPLC.

The amount of lipase used is about 5 g/l to about 50 g/l; preferably it is about 15 to 25 g/l The concentration of the substrate may be from 0.1 g/l to about 45 g/l. The surfactant may be used from about 0.05% to about 5%, preferably about 0.1% to about 0.5% by volume. The enzyme may be used as crude preparation isolated from the producing organism, in the commercially available form, or it may be immobilized on solid support.

The desired hydrolysis product, the unreacted substrate ester, and the enzyme may be recovered from the hydrolysis mixture using convential techniques such as filtration, chromatography, crystallization, or combinations thereof. The recovered enzyme may be used in subsequent hydrolysis, and the recovered ester may be racemized and also reused.

The enzymatic hydrolysis of the present invention is illustrated as follows using the benzyl ester of formula II as the substrate, and Amano lipase PS-800 as the enzyme. The hydrolysis in this case shows a kinetic profile that indicates a poisoning of the enzyme activity after about 96 hr, with a falloff in significant acid production. In addition, the profile of the enantioselectivity in the production of the desired acid shows a gradual diminishment from an initial enantiomeric excess (e.e.) of about 95% to about 88% e.e. over a 7 day hydrolysis experiment. The optimal time cycle for the hydrolysis using the above combination of substrate and enzyme, in terms of production (about 25%) of acid with high enantioselectivity (about 93% e.e.), occurs at approximately 96 hr.

The hydrolysis, performed in aqueous phosphate buffer in the presence of Triton X-100 at 37° C., is heterogeneous in terms of the benzyl ester and enzyme, while the acid and benzyl alcohol produced are solubilized. Filtration of the hydrolysis mixture after a 96 hr age through a coarse scintered glass funnel, overlaid with filter paper, readily removed the benzyl ester. The mixture was then filtered through a Millipore 10 kilo-Dalton regenerated cellulose filter cartridge, which retained the enzyme and permeated the aqueous solution containing the desired (S)-acid, phosphate buffer, Triton X-100 and benzyl alcohol. The enzyme was recovered free of salts, Triton X-100 and benzyl alcohol, retained >90% of the original activity in the olive oil assay, and was ready for reuse. The aqueous permeate retained little or no enzyme activity. Filtration of the enzyme through a 30 kD filter cartridge resulted in enzyme activity equally partitioned between the retentate and permeate.

Isolation of the (S)-acid from the permeate was achieved by isopropyl acetate extraction of the aqueous phase after adjustment to pH 5 with 5% phosphoric acid and the addition of sodium chloride. Evaporation and crystallization from t-butyl methylether (MTBE) resulted in a 90% recovery of acid 2 with 93% e.e.

Recovered benzyl ester (S:R enantiomer ratio 30:70) was racemized at 40° C. as a homogeneous solution in 90% aqueous acetonitrile in the presence of about 15 mol % benzyl 4-hydroxy benzoate and about 15 mol % cesium carbonate. Isolated racemic benzyl ester was resubmitted to enzyme hydrolysis using enzyme recovered from previous hydrolysis runs. Normal hydrolysis kinetics, acid production, and enantioselectivity were observed.

Utility

The (S)-azetidinone acid of formula I is an intermediate used in the preparation of elastase inhibitors of formula 1. The following scheme, using the compound of formula 2 as an example, depicts one possible route for the preparation of a compound of formula 1. The reaction sequence is generally disclosed in EP 337,549 and EP 595,557.

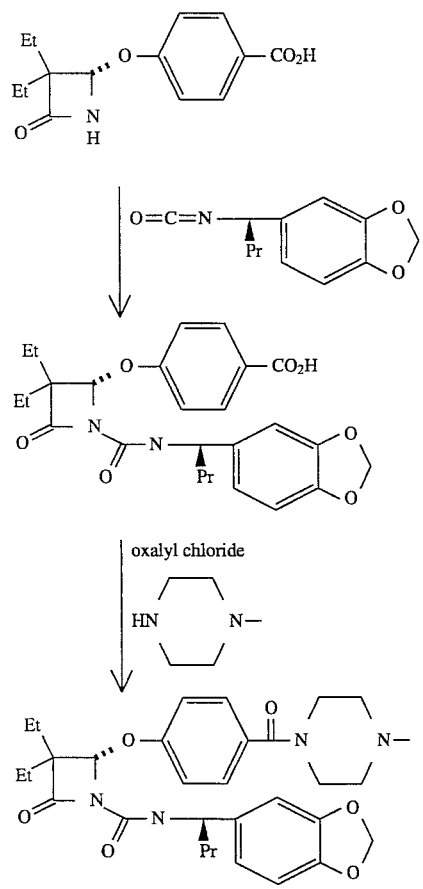

Thus, the carbamoyl moiety is added to the azetidinone nitrogen atom by treating the azetidinone acid with an appropriate isocyanate in the presence of a base such as triethylamine. The resulting β-lactam urea acid, in the presence of a coupling agent such as dicyclohexylcarbodiimide, or converted to an acylating equivalent thereof such as the acid chloride, is reacted with an appropriate amine, for example piperazine, to provide the final product. It will be appreciated that the two reaction steps shown may be performed in reversed order, i.e. the carboxylic acid is first converted to the amide, and the carbamoyl moiety added in the second step.

The following examples are provided to more fully illustrate the invention as claimed, and are not to be construed as limiting the scope of the invention.

EXAMPLE 1

Enzyme Hydrolysis of 3,3-diethyl-4[(4'-benzyloxycarbonyl)phenoxy]-2-azetidinone

The benzyl ester, 3,3-diethyl-4-[(4'-benzyloxycarbonyl)-phenoxy]-2-azetidinone (43 g), as a racemic mixture, was added to a 0.1M phosphate buffered aqueous solution (1.5 L, pH 7.7) of Triton X-100 (4.5 mL) and stirred (200 RPM) at 37° C. for 30 min. Lipase PS-800 (30 g), as a powder, was added and the mixture was agitated for 96 hr. HPLC assay of the broth indicated that approx. 8 g of the acid (4S)-3,3-diethyl-4-[(4'-carboxy)phenoxy]-2-azetidinone was produced. (HPLC assay conditions: Inertsil C8, acetonitrile: 0.1% H3PO4, gradient 25:75 to 100:0 over 20 min, 25° C., 2.0 mL/min, 242 nm. Retention time: acid 7.0 min; ester 13.5 min).

Samples were withdrawn at various times, extracted with methylene chloride and assayed by chiral SFC-HPLC (SFC= supercritical fluid chromatography) to determine the enantioselectivity of the hydrolysis. Chiral SFC-HPLC: Chiracel OD(H) (made by Chiral Technologies), 28 vol % EtOH (containing 20 mM HCl04), 1.0 mL/min, 300 Bar, 35° C. Retention time: (S)-acid–7.6 min; (S)-ester–8.3 min; (R)-acid–9.5 min; (R)-ester–11.6 min.

EXAMPLE 2

Isolation of benzyl ester, (S)-acid and enzyme

The enzyme hydrolysis mixture (from Example 1, 1.5L), containing suspended benzyl ester and enzyme, and dissolved (S)-acid (8.09 g), was filtered through a coarse scintered glass funnel that was overlaid with filter paper. The ester was washed with water (3×200 mL), dried, and set aside for racemization, and the combined aqueous layers were filtered through a 10 kilo-Dalton membrane filter.

The aqueous suspension of the enzyme in the hydrolysis medium was pumped (Cole-Parmer Masterflex centrifugal pump) at ~300 mL/min through a Millipore PLTK Prep/Scale-TFF 1 ft² 10 k regenerated cellulose filter cartridge (catalogue number CDUF001LT 10 k). The retentate return line was restricted to allow a permeate flow of ~700 mL/hr. When the enzyme slurry was filtered through a 30 kilo-Dalton filter, half of the enzyme activity remained with the permeate.

When the retentate volume in the flask was reduced to 50 mL it was diluted with water (3×250 mL) to prevent clogging of the filter cartridge at the end of the filtration. The final reduction in volume was followed by a dilution to 250 mL with water and recirculation of the enzyme slurry through the filter. The enzyme slurry was removed and drained from the filter and fresh water (250 mL) was recirculated through the filter (twice) to recover the enzyme. The combined aqueous enzyme washes were set aside for assay and reuse in the subsequent enzyme hydrolysis. Assay of the recovered aqueous enzyme suspension (olive oil hydrolysis) indicated that 90% activity of enzyme was recovered.

The permeate (3 L) was treated with 5% phosphoric acid to adjust the pH to 5.0, then sodium chloride (1.2 Kg) was added and the mixture was extracted with isopropyl acetate (3×200 mL). The bulk of the aqueous phase was removed and the remainder required filtration through a scintered glass funnel to remove interfacial material which prevented clean separation of the two phases.

The combined extracts were washed with water (200 mL), evaporated to 200 mL volume and diluted to 500 mL with dry isopropyl acetate. The material was reconcentrated to 200 mL volume to azeotropically dry the solution and then filtered to remove inorganic solids. The solution was combined with a second solution obtained from Example 1 (8.8 g acid), which used the recovered enzyme from Example 1 and so demonstrated the ability to recycle the enzyme, and the combined solution was evaporated to a solid. This material was dissolved into refluxing methyl t-butyl ether (MTBE, 200 mL), then evaporated in vacuo to ~100 mL. The material began crystallizing during concentration and was aged at 20° C. for 5 hr. The mixture was filtered, washed with MTBE and dried to give 13.5 g of solids. The mother liquours were concentrated to 30 mL vol, aged for 5 hr, filtered, washed with MTBE and dried to give an additional 2.05 g of material. The solids were assayed by HPLC and found to be 91 wt % pure and 96 wt %, resp., for a total of 14.2 g of (4S)-3,3-diethyl-4-[(4-carboxy)phenoxy]2-azetidinone (84% recovery, 1.78 g in M.L.), with a 93% e.e. by chiral SFC-HPLC assay.

EXAMPLE 3

Racemization of benzyl ester

Benzyl ester (55.8 g, 92 wt %, 51.3 g by HPLC), recovered from enzyme hydrolyses as a 70:30 mixture of R:S enantiomers, was added to acetonitrile: water (90:10, 165 mL) at 20° C. and warmed to 50° C. to give a homogeneous solution. To the solution, benzyl 4-hydroxybenzoate (0.38 g) and cesium carbonate (0.5 g) was added. This solution was then heated and aged at 50–55° C. for six hours.

After cooling the reaction mixture to room temperature, water (500 mL) was added and the aqueous phase was extracted with MTBE (2×100 mL). The combined organic phase was washed with sat aq NaCl (50 mL) then concentrated in vacuo (40° C., 28 in of Hg) to a volume of ~80 mL. This was then diluted with ethanol (75 mL) evaporated to ~80 mL then diluted with ethanol to 150 mL volume whereupon the benzyl ester began to slowly crystallize after seeding. Water (100 mL) was added dropwise over 1 hr, the mixture was aged for 1 hr, then filtered. The ester was washed with ethanol: water (100 mL, 2:1) and dried in vacuo (45° C., 20 hr) to give 45.2 g of crystalline material. The ester was assayed to be 98.7 wt % by HPLC assay, for a recovery of 87%. The mother liquour was assayed and found to contain 3.3 g of ester. HPLC assay: Inertsil C8 (250×4.6 mm), 5μ, acetonitrile: 0.1 v% aq $HClO_4$ gradient: 25:75 to 100:0 over 20 min, 2.0 mL/min, 25° C., 238 nm. Retention time: benzyl 4-hydroxybenzoate 10.4 min benzyl ester 13.4 min

What is claimed is:

1. A method for producing optically active (S)-azetidinone acid of the formula I

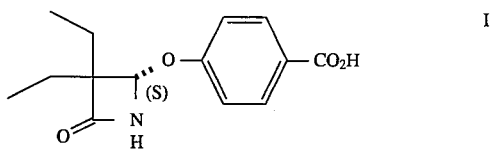

which comprises contacting a racemic mixture of an ester of formula II

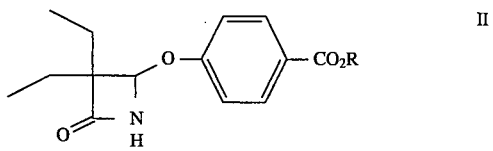

wherein R is selected from benzyl and $C_1$–$C_8$ alkyl, with a lipase obtained from *Pseudomonas aeruginosa* or with lipase PS, in the presence of a surfactant, and recovering said (S)-azetidinone acid.

2. A method of claim 1 wherein said lipase is obtained from Pseudomonas aeruginosa MB 5001, (ATCC 55162).

3. The method of claim 1 wherein R of the ester of formula II is benzyl.

4. The method of claim 1 wherein said surfactant is octylphenoxy polyethoxyethanol.

* * * * *